US010549003B2

(12) United States Patent
Chauhan et al.

(10) Patent No.: US 10,549,003 B2
(45) Date of Patent: Feb. 4, 2020

(54) METHOD OF DEMONSTRATING EFFICACY OF A MALODOR COUNTERACTANT PRODUCT

(71) Applicant: The Procter & Gamble Company, Cincinnati, OH (US)

(72) Inventors: Garima Chauhan, Singapore (SG); Tomoko Shindo, Singapore (SG)

(73) Assignee: The Procter & Gamble Company, Cincinnati, OH (US)

(*) Notice: Subject to any disclaimer, the term of this patent is extended or adjusted under 35 U.S.C. 154(b) by 260 days.

(21) Appl. No.: 15/598,411

(22) Filed: May 18, 2017

(65) Prior Publication Data

US 2017/0340763 A1 Nov. 30, 2017

Related U.S. Application Data

(60) Provisional application No. 62/343,138, filed on May 31, 2016.

(51) Int. Cl.
*A61L 9/00* (2006.01)
*G01F 3/02* (2006.01)
(Continued)

(52) U.S. Cl.
CPC ............... *A61L 2/28* (2013.01); *G01N 31/22* (2013.01); *A61L 2202/26* (2013.01)

(58) Field of Classification Search
CPC ........... A61L 9/00; A61L 2209/10; A61L 9/04
(Continued)

(56) References Cited

U.S. PATENT DOCUMENTS 3,960,494 A * 6/1976 Verma .................. G01N 31/223
436/120
2005/0112085 A1* 5/2005 MacDonald ............ A61F 13/42
424/76.1
2005/0201971 A1 9/2005 Janardanan Nair et al.

FOREIGN PATENT DOCUMENTS

WO WO 2005/039656 A1 5/2005
WO WO2005/086806 A2 9/2005
(Continued)

OTHER PUBLICATIONS

PCT Search Report PCT/US2017/034127; dated May 24, 2017; 14 Pages.

*Primary Examiner* — Monzer R Chorbaji
(74) *Attorney, Agent, or Firm* — Abbey A. Lopez

(57) ABSTRACT

A method of demonstrating efficacy of a malodor counteractant product, the method comprising the steps of:
a) treating one of two odorous fabric articles with a malodor counteractant product, wherein the two odorous fabric articles comprise a malodor compound and are treated with a color indicator wherein the color indicator is configured to change color upon interaction with a malodor compound;
b) providing the treated one of the two odorous fabric articles in a first enclosed environment comprising one of two odorless fabric articles, wherein the two odorless fabric articles are treated with the color indicator;
c) providing the other one of the two odorous fabric articles in a second enclosed environment comprising the other one of two odorless fabric articles; and
d) allow the odorous and odorless fabric articles to remain in the first and second enclosed environments for a period of time sufficient to cause a difference of color between the one of two odorless fabric articles in the
(Continued)

first enclosed environment and the other one of the two odorless fabric articles in the second enclosed environment.

**13 Claims, 6 Drawing Sheets
(1 of 6 Drawing Sheet(s) Filed in Color)**

(51) Int. Cl.
*A61L 2/28* (2006.01)
*G01N 31/22* (2006.01)
(58) Field of Classification Search
USPC .... 422/5, 83, 120, 123, 306; 424/76.1, 76.5, 424/76.8; 73/232; 206/459.1
See application file for complete search history.

(56) References Cited

FOREIGN PATENT DOCUMENTS

WO    WO 2006/076821 A1    7/2006
WO    WO 2016/120165 A1    8/2016

\* cited by examiner

METHOD OF DEMONSTRATING EFFICACY OF A MALODOR COUNTERACTANT PRODUCT

FIELD OF THE INVENTION

The invention relates to a method of demonstrating efficacy of a malodor counteractant product and a kit adapted for demonstrating the method.

BACKGROUND OF THE INVENTION

Malodors are offensive odors which exist in the air and on many substrates such as fabrics, and hard surfaces. Chemicals which contribute to household and environmental malodors include, for example, ammonia, amines, thiols, sulfides, short chain aliphatic and olefinic acids, e.g. fatty acids.

Deodorizers such as air and fabric freshenening products have been developed to counteract such malodors. However, as malodors are generally invisible, it is difficult to show the malodor removal performance of a deodorizer to consumers on television or on the internet.

International Application No. PCT/US2005/007553 (WO 2005/086806A2) describes an advertisement method for advertising a deodorizer. The method comprises the steps of preparing a deodorizer product to be advertised or promoted ("promotion product") and a different deodorizer product ("comparative product"), preparing at least two separate closed spaces, and then, in any order: placing the promotion product inside one of the closed spaces; placing a material comprising a color indicator inside each closed space, wherein the material includes paper, a fabric, a non-woven material and/or plastic; and adding a malodor substance to each of the closed spaces to thereby cause a color change to the color indicator.

However, there remains a need for a method of demonstrating efficacy of a malodor counteractant product.

SUMMARY OF THE INVENTION

The present invention relates to a method of demonstrating efficacy of a malodor counteractant product, the method comprising the steps of:
  a) treating one of two odorous fabric articles with a malodor counteractant product, wherein the two odorous fabric articles comprise a malodor compound and are treated with a color indicator wherein the color indicator is configured to change color upon interaction with a malodor compound;
  b) providing the treated one of the two odorous fabric articles in a first enclosed environment comprising one of two odorless fabric articles, wherein the two odorless fabric articles are treated with the color indicator;
  c) providing the other one of the two odorous fabric articles in a second enclosed environment comprising the other one of two odorless fabric articles; and
  d) allowing the odorous and odorless fabric articles to remain in the first and second enclosed environments for a period of time sufficient to cause a difference of color between the one of two odorless fabric articles in the first enclosed environment and the other one of the two odorless fabric articles in the second enclosed environment.

Exposing fabrics with malodor to fabrics without malodor will often result in the fabrics with malodor releasing malodor to other clean fabrics and contribute to malodor in an enclosed space. Specifically, when the fabrics with malodor are brought close to other clean fabrics, the malodor is transferred to those fabrics thereby contaminating them. This results in easy visualization of how the fabrics laden with malodor are able to contaminate other clean fabrics and hence create a cycle of odor and that when fabrics laden with malodor are sprayed with a malodor counteractant product, the malodor is neutralized and/or absorbed and cannot contaminate other clean fabrics. As a result, the cycle of odor is significantly reduced or stopped altogether.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Malodor counteractant products have been used to eliminate malodor present on fabrics and in closed spaces which consumers occupy such as houses, and vehicles. The present invention is directed to a method of visualizing efficacy of a malodor counteractant product and a kit for demonstrating the method.

As used herein, the term "closed space" comprises a substantially enclosed volume of space in a domestic, commercial or vehicle environment.

As used herein, the term "malodor counteractant product" comprises a product comprising a malodor counteractant ingredient for removing malodors from fabric articles and/or from air in a closed space by absorption of or by neutralizing the malodors. Non-limiting examples of suitable malodor counteractant products comprise odor control compositions that are commercially available and sold under the trade names Febreze® and Febreze Fabric Refresher™.

Figure 1:
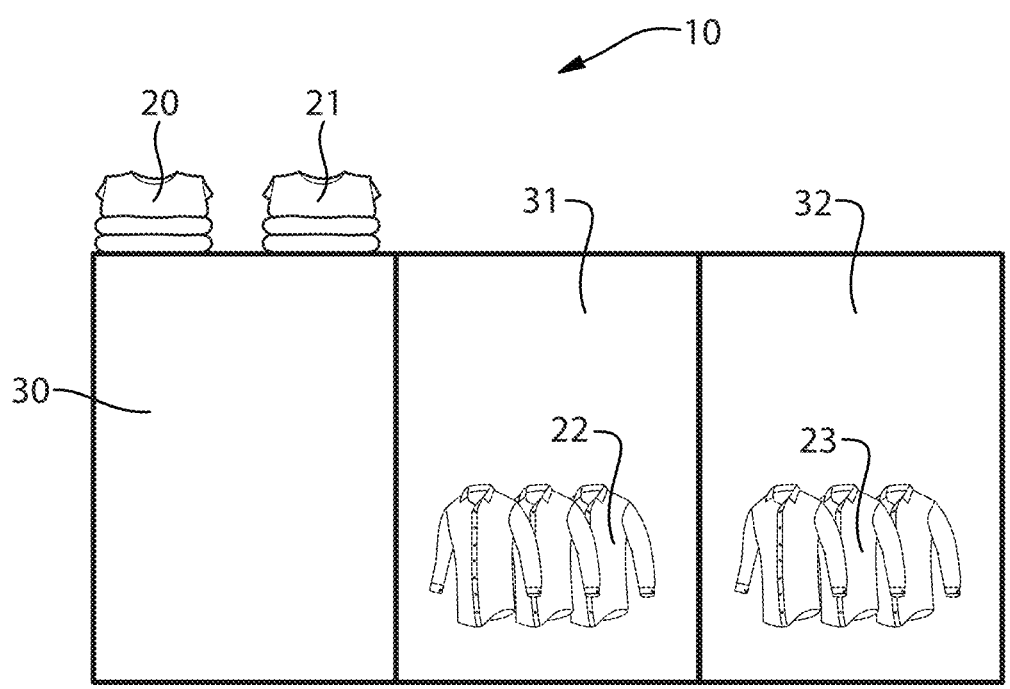
FIG. 1 is a schematic view of a kit for demonstrating a method of demonstrating efficacy of a malodor counteractant product.
Figure 3A:
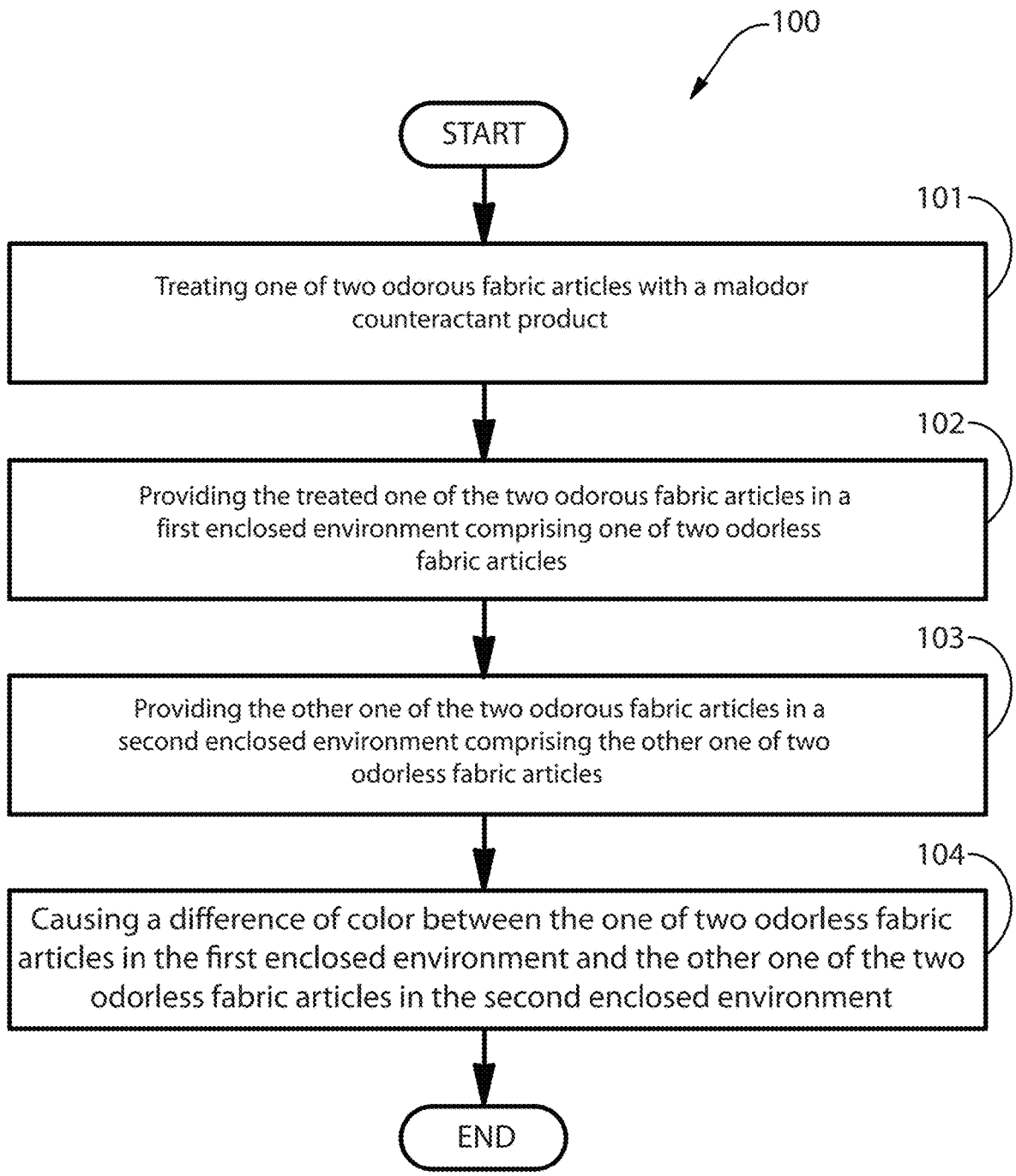
FIG. 3A is a flow chart of a method of demonstrating efficacy of a malodor counteractant product.

FIG. 1 is a schematic view of a portable kit 10 for demonstrating a method 100 of demonstrating efficacy of a malodor counteractant product according to the present invention and FIG. 3A is a flow chart of the method 100. The kit 10 may be a point of sale material (POSM) to be used for as a fixed display in stores for demonstrating the method 100 or a portable display. As shown in FIG. 1, the kit 10 comprises a first fabric article 20, a second fabric article 21, a first chamber 30 for receiving the first and second fabric articles 20, 21, a second chamber 31 comprising a third fabric article 22, and a third chamber 32 comprising a fourth fabric article 23. The chambers 30, 31, 32 may be configured to be separate units sized and configured for portability and ease of transportation between different locations or integral to form a single unit with separate chambers if used as a POSM in stores.

Each of the chambers 30, 31, 32 defines a closed space respectively for receiving at least two fabric articles. Each chamber 30, 31, 32 may comprise a length L, width W and height H and the volume of the closed space may vary depending on size of the fabric articles placed within the closed space.

The chambers 30, 31, 32 may comprise a transparent or translucent material so that any color changes may be viewed from outside the closed space.

The first, second, third and fourth fabric articles 20, 21, 22, 23 may be pre-treated with a color indicator capable of exhibiting a color change upon exposure to a malodor compound. It will be appreciated that the malodor compound may belong to either acidic or base type malodor and the color indicator may be selected accordingly to enable visual detection of the malodor compound. For example, the malodor compound may comprise a malodor substance selected from the group consisting of: ammonia, bacteria, thiols, aldehydes, amines, sulfides, fatty acids, alcohols, and mixtures thereof.

Figure 2:
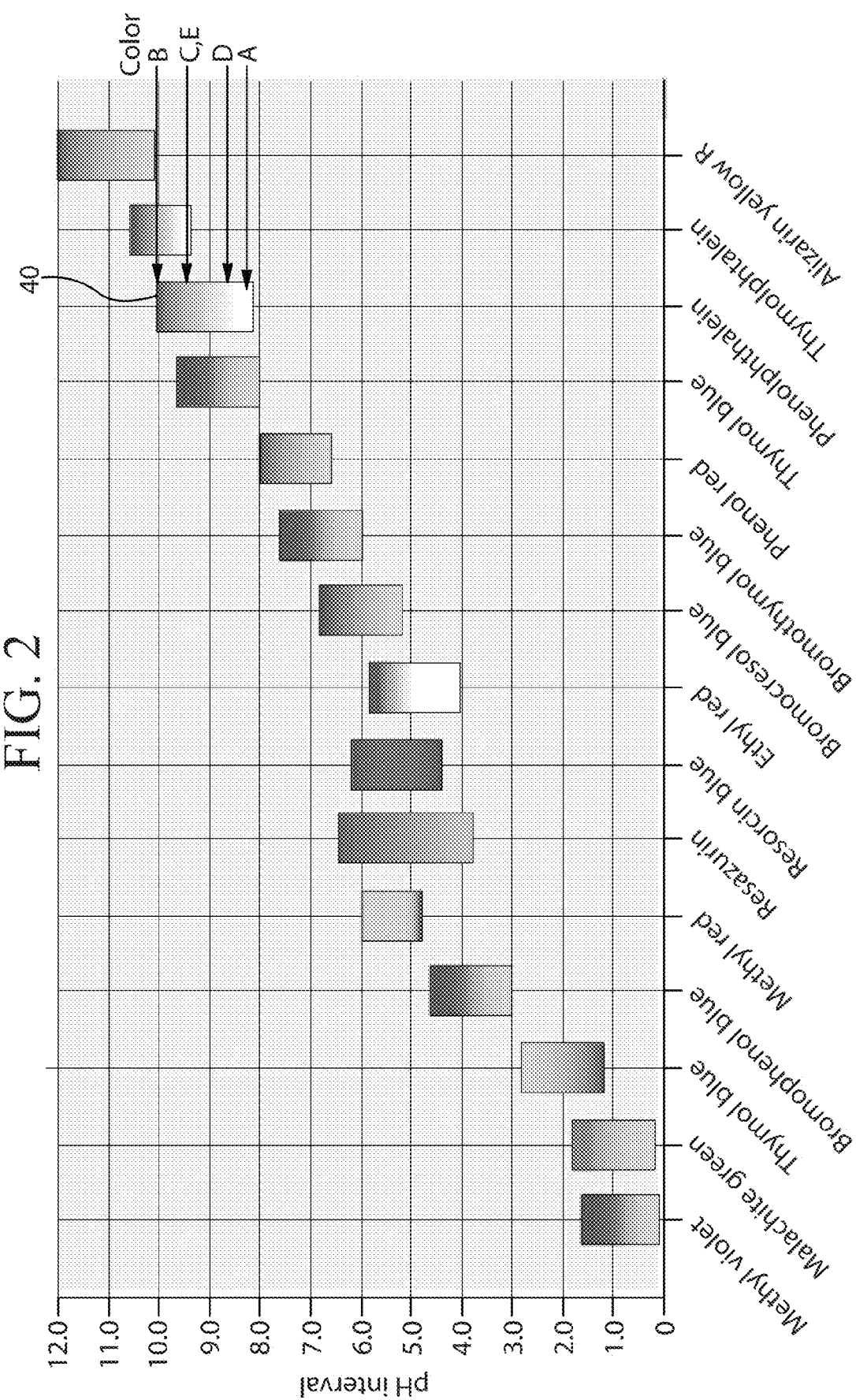
FIG. 2 is a graph showing a relationship between color indicators and an approximate pH range over which the color indicator change color and their change in color.

The color indicator may comprise a pH sensitive dye selected from the group consisting of: bromocresol green, bromocresol purple, methyl orange, methyl red, bromothymol blue, thymol blue, phenol red, neutral red, cresol red, cresolphthalein, naphtholphthalein, phenolphthalein, thymolphthalein. FIG. 2 is a graph showing a relationship between color indicators and an approximate pH range over which the color indicator change color and their change in color.

Specifically, when the malodor compound interacts with the color indicator present in the fabric articles, the color indicator changes color from a low pH color to a high pH color to indicate the increase in the pH level caused by the malodor compound.

The third and fourth fabric articles 22, 23 may be detachably attached within the second and third chambers 31, 32 respectively. Prior to performing the method 100, the first, second, third and fourth fabric articles 20, 21, 22 and 23 are substantially free from malodor ("odorless") and may comprise a first color such as white.

Prior to performing the method 100 as shown in FIG. 3A, the first and second fabric articles 20, 21 may be exposed to a malodor compound to form two odorous fabric articles 20, 21. The malodor compound may comprise a color indicator such as a pH-sensitive dye for causing the malodor compound to exhibit a color visible to the naked eye. The third and fourth fabric articles 22, 23 remain as odorless fabric articles Referring to FIG. 3A, the method 100 comprises treating one of the odorous fabric articles 20, 21 is treated with a malodor counteractant product 13 (shown in FIG. 3D) whereas the other one of the odorous articles 20, 21 is untreated. The color of the malodor compound is different from the first color of the first, second, third and fourth fabric articles 20, 21, 22, 23 to enable consumers to visualize the malodor compound. The treated one of the two odorous fabric articles 20, 21 is provided 102 in a first enclosed environment comprising one of two odorless fabric articles 22, 23. The other one of the two odorous fabric articles 20, 21 is provided 103 in a second enclosed environment comprising the other one of the two odorless fabric articles 22, 23. The odorous and odorless fabric articles 20, 21, 22, 23 are incubated in their respective environments for a predetermined period of time sufficient to cause 104 a difference of color between the one of two odorless fabric articles in the first enclosed environment and the other one of the two odorless fabric articles in the second enclosed environment In the present invention, neither of the odorless fabric articles 22, 23 are directly exposed to malodor yet it is anticipated that one of these odorless fabric articles 22, 23 will experience a color change. Specifically, there is a change in color in the odorless fabric article 22, 23 from a first color to a second color as soon as malodor from the untreated odorous fabric article 20, 21 comes into contact with the odorless fabric article 22, 23. The method 100 illustrates the benefit of treating an odorous fabric with a malodor counteractant product to stop transfer of malodor from fabric to fabric. Specifically, in step 101, the malodor counteractant product neutralizes the pH level of the malodor compound present and controls the malodor from evaporating from the treated odorous fabric article and transferring to the odorless fabric article.

Figure 3B:
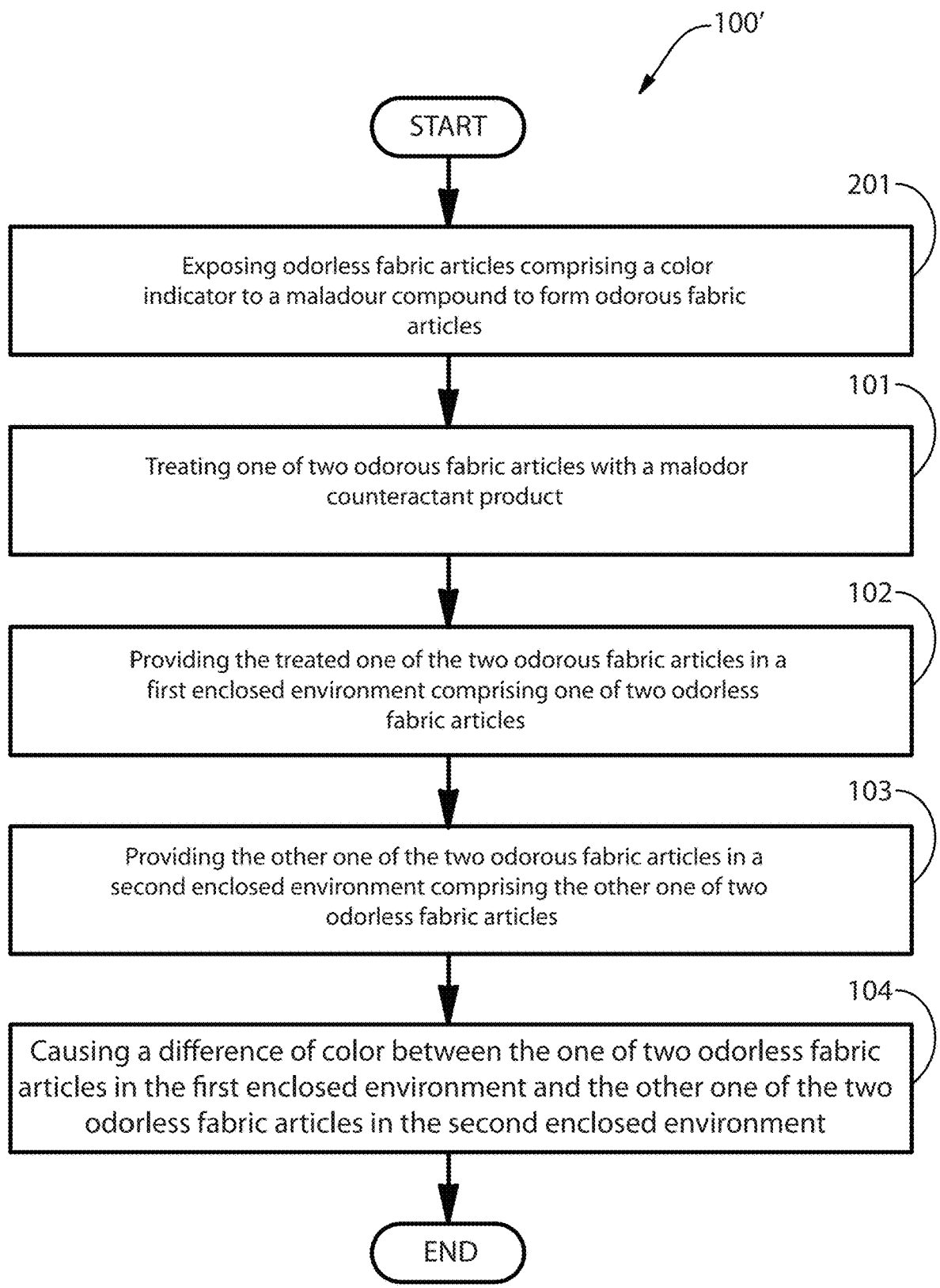
FIG. 3B is a variation of the method of FIG. 3A.

FIG. 3B shows a flowchart of a variation of the method 100 of FIG. 3A wherein in addition to the steps 101, 102, 103, 104 of the method 100, a method 100' comprises exposing 201 odorless fabric articles comprising a color indicator to a malodor compound to form odorous fabric articles and Treating one of the odorous fabric articles with a malodor counteractant product.

The method 100 may be suitable for use in recording demonstrations to be shown as TV copy as the number of steps is less than the number of steps in the method 100'. An advantage is that this reduces the number of frames to be shot and air time and accordingly reduces advertisement costs. The method 100' may be suitable for use for educating consumers in on-site product demonstrations.

The method 100 for demonstrating efficacy of a malodor counteractant product in accordance with the present invention may be carried out as described below. Specifically, FIGS. 4A to 4G show a process flow diagram illustrating a visual demonstration of efficacy of a malodor counteractant product.

Figure 4A:
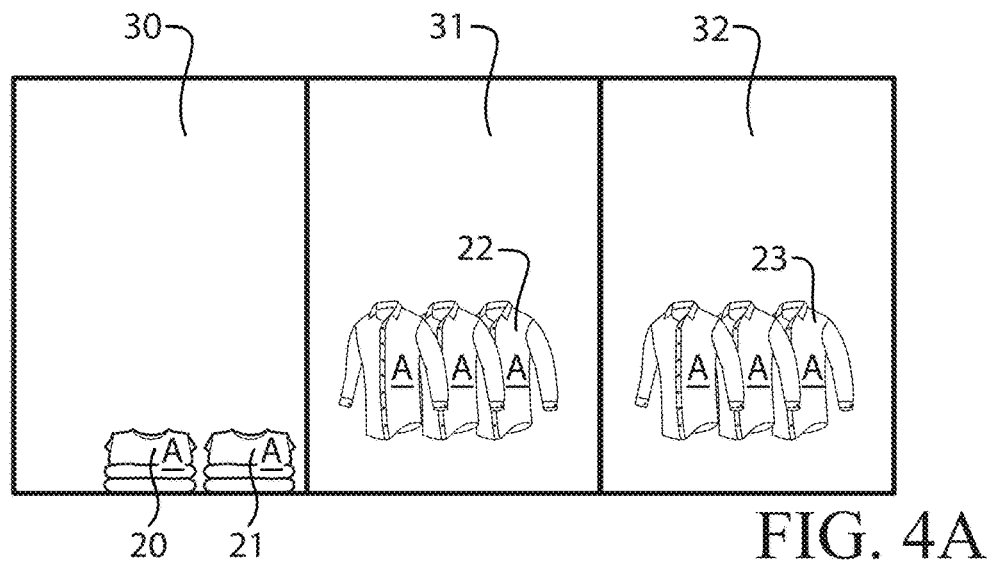
FIGS. 4A to 4G is a product demonstration process diagram for demonstrating efficacy of a malodor counteractant product.

As shown in FIG. 4A, the first and second chambers 30, 31 are adjacent to each other and the third chamber 32 is adjacent to the second chamber 31. The second chamber 31 comprises the third fabric article 22 and the third chamber 32 comprises the fourth fabric article 23. The first and second fabric articles 20, 21 are placed in the first chamber 30. The first, second, third and fourth fabric articles 20, 21, 22, 23 are treated with a color indicator such as phenolphthalein having a pH color range 40 as shown in FIG. 2 and comprise a first color A in the pH color range 40.

Figure 4B:
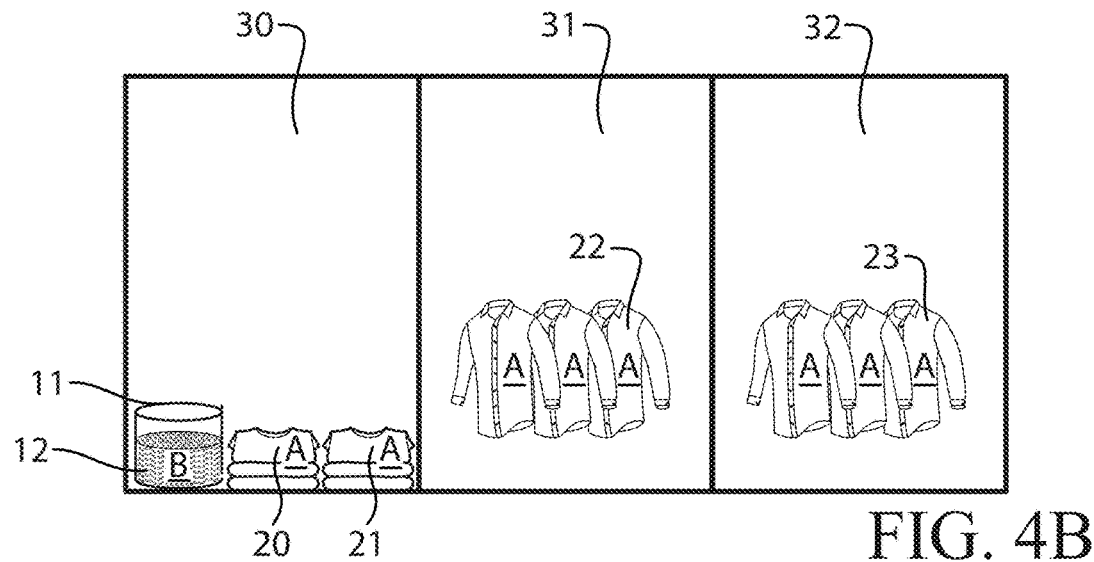

As shown in FIG. 4B, a beaker 11 of malodor compound 12 is placed in the first chamber 30 containing the first and second fabric articles 20, 21 for a time period of about 3 minutes. The malodor compound may be configured so as to exhibit a bright pink color B whereas the first color A of the fabric articles 20, 21, 22, 23 is white. This is enable clear visualization of any transfer of the malodor compound to the first and second fabric articles 20, 21 to form odorous first and second fabric articles 20, 21.

Figure 4C:
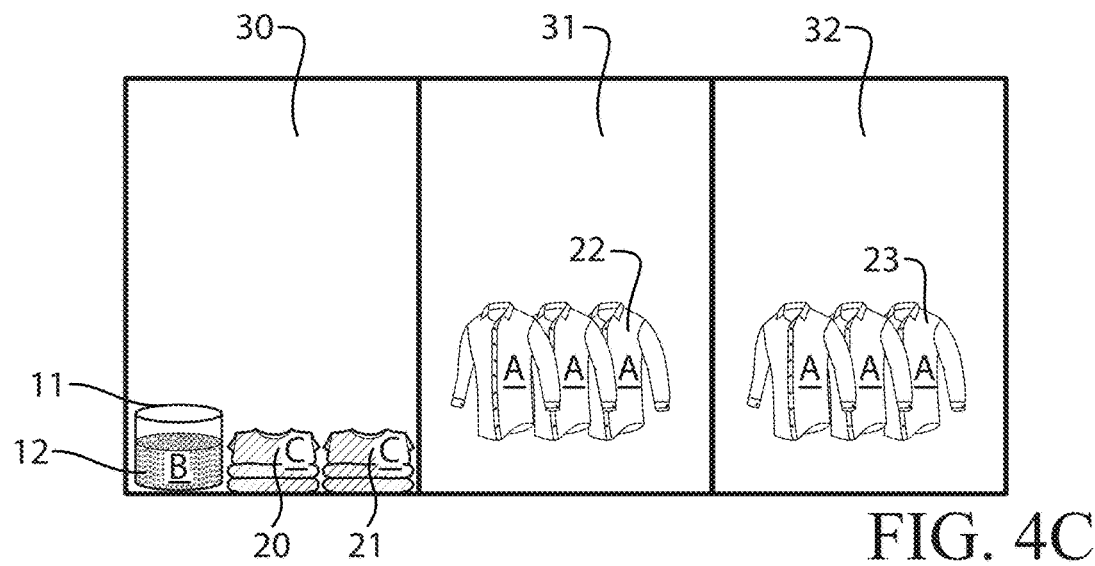

Specifically, FIG. 4C show that that the change of color of the first and second fabric articles 20, 21 from the first color A to a second color C due to malodor particles reacting with the color indicator present in the first and second fabric articles 20, 21. The second color C may correspond to the color B of the malodor compound 12. Specifically, the first and second fabric articles 20, 21 have absorbed malodor which is released from the beaker 11 containing the malodor compound 12 into the air within the first chamber 30.

Figure 4D:
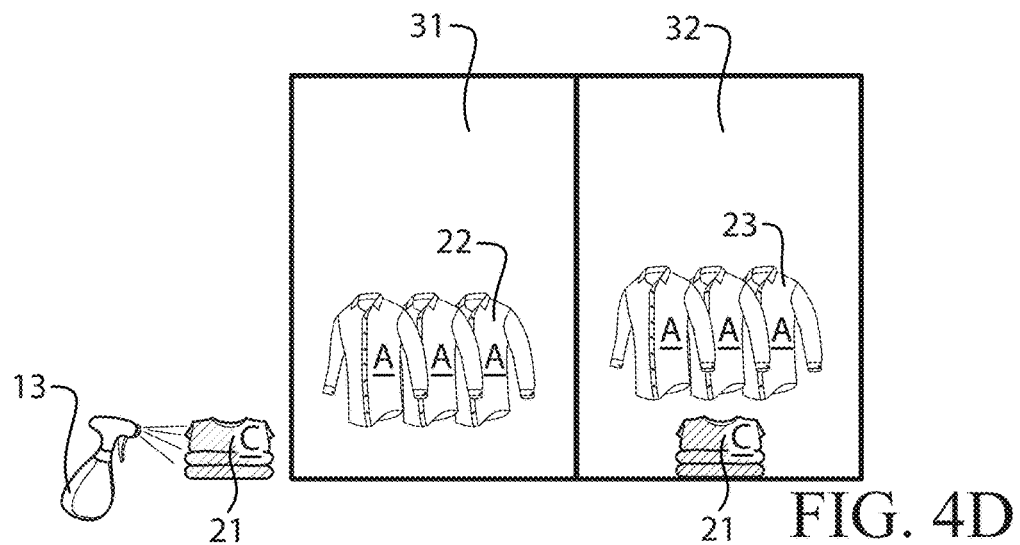
Figures 4E, 4F:
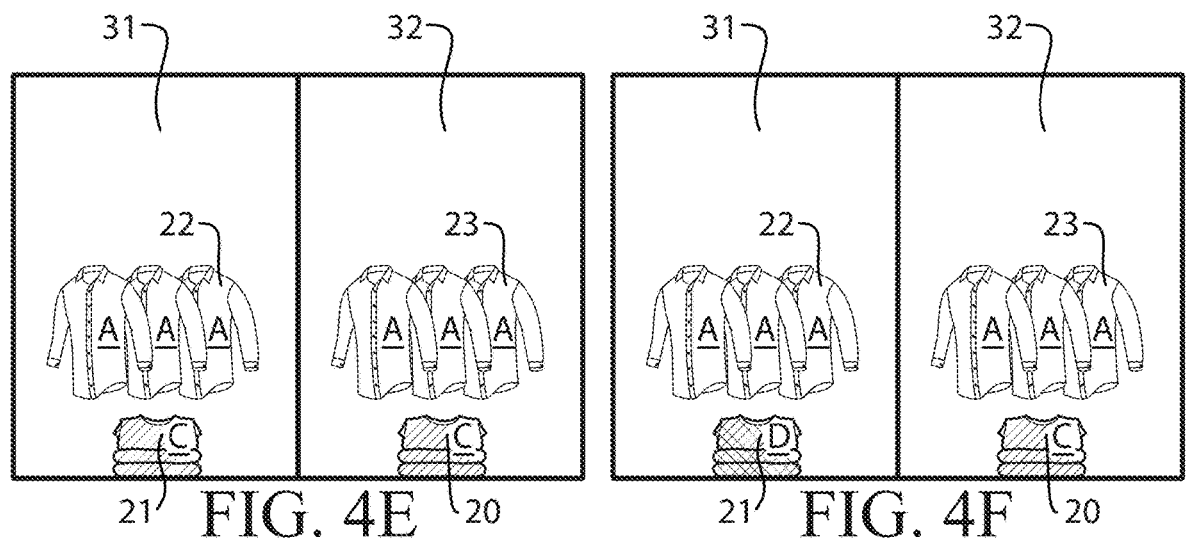

Referring to FIG. 4D, the odorous first fabric article 20 is removed from the first chamber 30 and placed in the third chamber 32 comprising the fourth fabric article 23. The odorous second fabric article 21 is removed from the first chamber 30 and treated with a malodor counteractant product 13 prior to placement in the second chamber 31 comprising the third fabric article 22 as shown in FIG. 4E. The malodor counteractant product 13 may be provided in a spray bottle. For example, the odorous second fabric article 21 may be sprayed five times with the malodor counteractant product 13 to ensure a sufficient amount of the malodor counteractant product to counteract the malodor.

Referring to FIG. 4F, the third and fourth fabric articles 22, 23 were incubated for period of 3 to 5 minutes. A color change from the second color C to a third color D in the second fabric article 21 is caused due to treatment with the malodor counteractant product 13 which neutralizes the pH of the malodor thereby resulting in the color change in the color indicator.

Figure 4G:
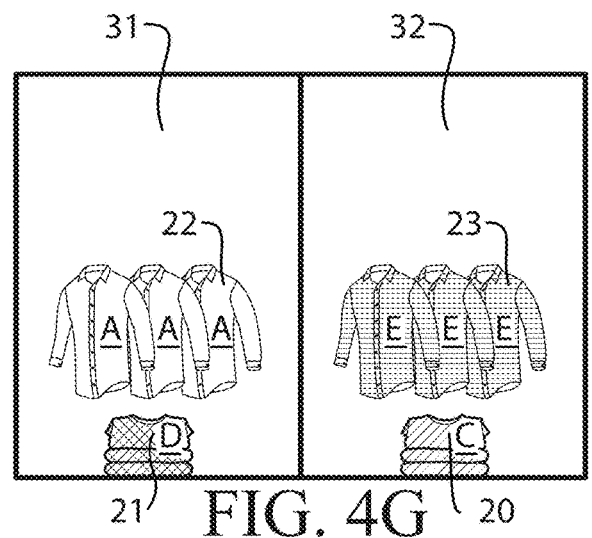

Referring to FIG. 4G, a color change from the first color A to a second color E is generated in the fourth fabric article 23 because of the untreated odorous first fabric article 20 comprising malodor which is re-evaporated into the third chamber 32 and transferred onto the fourth fabric article 23. No color change is generated in the third fabric article 22 which demonstrates that the malodor counteractant product applied on the odorous second fabric article 21 has prevented the malodor compound present on the second fabric article 21 from being released into the air and therefore malodor is not transferred to the third fabric article 22. A color change may also be generated in the odorous second fabric article 21 due to a malodor counteractant in the malodor counteractant product reacting with the malodor compound to neutralize the malodor compound. Colors C, D, E may be within the limits of colors A and B of the color range 40 as shown in FIG. 2.

An effect of exposing the odorless fabric articles to the malodor compound configured to be visible to the naked eye is to visually demonstrate through a color change that fabrics are responsible for absorbing and re-emitting malodor hence creating a cycle of odor in a closed space such as in the house. A further effect of exposing fabrics with malodor to fabrics without malodor is to demonstrate fabrics with malodor release malodor to other clean fabrics and contribute to malodor in an enclosed space.

Specifically, as shown in FIG. 4G, when the fabrics with malodor are brought close to other clean fabrics, the malodor is transferred to those fabrics thereby contaminating them.

An advantage of the present invention is easy visualization and demonstration of how the fabrics laden with malodor are able to contaminate other clean fabrics and hence create a cycle of odor and that when fabrics laden with malodor are sprayed with a malodor counteractant product, the malodor is not released and cannot contaminate other clean fabrics. As a result, the cycle of odor is significantly reduced or stopped altogether.

Further, the present invention may be used in product demonstrations configured in the form of portable on-site displays or videos available on media platforms to raise awareness in consumers that fabrics laden with malodor are able to contaminate other clean fabrics and hence create a cycle of odor and what they need to do to counteract such malodor to improve hygiene in the spaces consumers occupy.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical name, or otherwise defined below.

Example 1

An experimental design set up for performing the present invention according to the methods 100, 100' and/or the process as shown in FIGS. 4A to 4G is illustrated in Table 1 which lists equipment and materials used in the present invention.

TABLE 1

| Equipment/Materials | Components |
|---|---|
| pH sensitive dye | Phenolphthalein |
| Malodor Compound | Solution of: Malodor chemical-1 ml of 28% Ammonia pH sensitive dye-2 drops of phenolphthalein (1% in Ethanol 50%) |
| Malodor counteractant product | Febreze Fabric Refreshener ™ |
| Container for Malodor Compound | Glass beaker (25 ml) |
| First Chamber | Acrylic chamber (25 cm × 20 cm × 30 cm) |
| Second Chamber | Acrylic chamber (25 cm × 20 cm × 30 cm) |
| Third Chamber | Polyacrylic chamber (25 cm × 20 cm × 30 cm) |
| First Fabric Article | Toy sofa covered with white fabric with pH sensitive dye |
| Second Fabric Article | Toy sofa covered with white fabric with pH sensitive dye |
| Third Fabric Article | Set of three miniature T-shirt cut outs (3 cm × 3 cm) made of white cotton, polyester, or blends thereof with pH sensitive dye |
| Fourth Fabric Article | Set of three miniature T-shirt cut outs (3 cm × 3 cm) made of white cotton, polyester, or blends thereof with pH sensitive dye |

Fabrics used in the present invention may comprise textile or fabrics used in household furniture or vehicle seats and may comprise one of: cotton polyester mix, silk, cotton, or mixtures thereof.

Further non-limiting examples of malodor compounds and corresponding malodor counteractant products for controlling the malodor compounds which are suitable for use in the present invention are described in detail in U.S. Pat. No. 5,942,217 published on Aug. 24, 1999, U.S. Pat. No. 5,955,093 published on Sep. 21, 1999, U.S. Pat. No. 6,033,679 published on Mar. 7, 2000, U.S. Pat. No. 6,106,738 published on Aug. 22, 2000, U.S. Pat. No. 6,284,231 published on Sep. 4, 2001, U.S. Pat. No. 5,997,759 published on Dec. 7, 1999, U.S. Pat. No. 6,987,099 published on Jan. 17, 2006, U.S. Pat. No. 6,656,923 published on Dec. 2, 2003, U.S. Pat. No. 6,528,013 published on Mar. 4, 2003, U.S. Pat. No. 5,968,404 published on Oct. 19, 1999, U.S. Pat. No. 6,767,507 published on Jul. 24, 2004, U.S. Pat. No. 6,878,695 published on Apr. 12, 2005, U.S. Pat. No. 6,503,413 published on Jan. 7, 2003, and U.S. Pat. No. 6,680,289 published on Jan. 20, 2004.

An example is shown below:

A. A method of demonstrating efficacy of a malodor counteractant product, the method comprising the steps of:
  a) treating one of two odorous fabric articles with a malodor counteractant product, wherein the two odorous fabric articles comprise a malodor compound and are treated with a color indicator wherein the color indicator is configured to change color upon interaction with a malodor compound;
  b) providing the treated one of the two odorous fabric articles in a first enclosed environment comprising one of two odorless fabric articles, wherein the two odorless fabric articles are treated with the color indicator;
c) providing the other one of the two odorous fabric articles in a second enclosed environment comprising the other one of two odorless fabric articles; and
d) allowing the odorless and odorous fabric articles to remain in the first and second enclosed environments for a period of time sufficient to cause f a difference of color between the one of two odorless fabric articles in the first enclosed environment and the other one of the two odorless fabric articles in the second enclosed environment.

B. The method of A further comprising, prior to step (a):
exposing two odorless fabric articles to a malodor compound to form two odorous fabric articles.

C. The method of A, wherein step (a) comprises:
spraying one of the two odorous fabric articles with the malodor counteractant product.

D. The method of A, wherein the malodor compound comprises the color indicator.

E. The method of A, wherein the malodor compound comprises a malodor substance selected from the group consisting of: ammonia, thiols, aldehydes, amines, sulfides, fatty acids, alcohols, and mixtures thereof.

F. The method of A, wherein the two odorous fabric articles comprise at least one fabric used in domestic, vehicle and/or personal articles.

G. The method of A, wherein step (b) comprises allowing the treated odorous fabric article to be in direct contact with the one of the two odorless fabric articles.

H. The method of A, wherein the step (c) comprises allowing the other one of the odorous fabric articles to be in direct contact with the other one of the two odorless fabric articles.

I. The method of A, further comprising generating, for display on a display, steps (a) to (d), wherein the display is a transparent window in each of the first and second enclosed environments.

J. The method of A, further comprising generating, for display on a display, steps (a) to (d), wherein the display is remote from the first and second enclosed environments, wherein the display is a display screen of a computing device or a television.

K. The method of A, wherein the malodor counteractant product comprises a malodor counteractant ingredient for absorbing or neutralizing the malodor compound.

L. The method of A, wherein the odorless and odorous fabric articles comprise one of: cotton polyester mix, silk, cotton, or mixtures thereof.

M. The method of A, wherein the malodor compound is a base type malodor substance and the color indicator is phenolphthalein.

N. A kit for demonstrating a method of demonstrating efficacy of a malodor counteractant product, the kit comprising:
a plurality of odorless fabric articles for treatment with a color indicator;
a first chamber for exposing two of the plurality of odorless fabric articles to a malodor compound to provide odorous fabric articles;
a second chamber for placing one of the odorous fabric articles with one of the plurality of odorless fabric articles; and
a third chamber for placing another one of the odorous fabric articles with another one of the plurality of odorless fabric articles, wherein one of the one or the another one of the odorous fabric articles are for treatment with a malodor counteractant product.

O. The kit of N, wherein at least one side of each of the first, second and third chambers comprise a transparent or a translucent material.

P. The kit of N, further comprising a malodor compound comprising a color indicator.

Q. The kit of N, wherein the odorless fabric articles comprise one of: cotton polyester mix, silk, cotton, or mixtures thereof.

R. A kit for demonstrating a method of visualizing efficacy of a malodor counteractant product, the kit comprising:
a plurality of odorless fabric articles pre-treated with a color indicator;
a plurality of odorous fabric articles pre-treated with the color indicator;
a first chamber for placing one of the plurality of odorless fabric articles with one of the plurality of odorous fabric articles treated with a malodor counteractant product;
a second chamber for placing another one of the plurality of odorless fabric articles with another one of the plurality of odorous fabric articles, wherein each of the first and second chambers comprise a transparent window for display a color change of the color indicator upon interaction with a malodor compound from one of the odorous fabric articles.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A method of demonstrating efficacy of a malodor counteractant product, the method comprising the steps of:
a) treating one of two odorous fabric articles with a malodor counteractant product, wherein the two odorous fabric articles comprise a malodor compound and are treated with a color indicator wherein the color indicator is configured to change color upon interaction with a malodor compound;
b) providing the treated one of the two odorous fabric articles in a first enclosed environment comprising one of two odorless fabric articles, wherein the two odorless fabric articles are treated with the color indicator;

c) providing the other one of the two odorous fabric articles in a second enclosed environment comprising the other one of two odorless fabric articles;

d) allowing the odorous and odorless fabric articles to remain in the first and second enclosed environments for a period of time sufficient to cause a difference of color between the one of two odorless fabric articles in the first enclosed environment and the other one of the two odorless fabric articles in the second enclosed environment; and e) assessing the difference in color to determine the level of malodor compound transferred to the two odorless fabrics.

2. The method of claim 1 further comprising, prior to step (a):
exposing two odorless fabric articles to a malodor compound to form two odorous fabric articles.

3. The method of claim 1, wherein step (a) comprises:
spraying one of the two odorous fabric articles with the malodor counteractant product.

4. The method of claim 1, wherein the malodor compound comprises the color indicator.

5. The method of claim 1, wherein the malodor compound comprises a malodor substance selected from the group consisting of: ammonia, thiols, aldehydes, amines, sulfides, fatty acids, alcohols, and mixtures thereof.

6. The method of claim 1, wherein the two odorous fabric articles comprise at least one fabric used in domestic, vehicle and/or personal articles.

7. The method of claim 1, wherein step (b) comprises allowing the treated odorous fabric article to be in direct contact with the one of the two odorless fabric articles.

8. The method of claim 1, wherein the step (c) comprises allowing the other one of the odorous fabric articles to be in direct contact with the other one of the two odorless fabric articles.

9. The method of claim 1, further comprising generating, for display on a display, steps (a) to (d), wherein the display is a transparent window in each of the first and second enclosed environments.

10. The method of claim 1, further comprising generating, for display on a display, steps (a) to (d), wherein the display is remote from the first and second enclosed environments, wherein the display is a display screen of a computing device or a television.

11. The method of claim 1, wherein the malodor counteractant product comprises a malodor counteractant ingredient for absorbing or neutralizing the malodor compound.

12. The method of claim 1, wherein the odorless and odorous fabric articles comprise one of: cotton polyester mix, silk, cotton, or mixtures thereof.

13. The method of claim 1, wherein the malodor compound is a base type malodor substance and the color indicator is phenolphthalein.

* * * * *